United States Patent [19]

Litman

[11] Patent Number: 4,554,820

[45] Date of Patent: Nov. 26, 1985

[54] METHOD AND APPARATUS FOR OBTAINING THE COMBINED AROMA OF SEVERAL SUBSTANCES

[76] Inventor: Ira Litman, 41 Holiday Park Dr., Hauppage, N.Y. 11788

[21] Appl. No.: 657,581

[22] Filed: Oct. 4, 1984

Related U.S. Application Data

[62] Division of Ser. No. 369,846, Apr. 19, 1982, Pat. No. 4,520,651.

[51] Int. Cl.⁴ .......................................... G01N 31/00
[52] U.S. Cl. ...................................................... 73/23
[58] Field of Search ................. 73/23, 27 R; 366/152, 366/160, 162; 426/131; 436/181

[56] References Cited

U.S. PATENT DOCUMENTS

| | | | |
|---|---|---|---|
| 2,837,912 | 6/1958 | Moncrieff | 73/23 |
| 3,686,930 | 8/1972 | Kniebes et al. | 73/23 |
| 3,882,713 | 5/1975 | Nishida et al. | 73/23 |
| 3,902,851 | 9/1975 | Dravnieks | 73/23 |
| 4,357,110 | 11/1982 | Hope et al. | 366/152 |
| 4,399,687 | 8/1983 | Collins | 73/23 |

Primary Examiner—Stephen A. Kreitman

[57] ABSTRACT

A method and apparatus for obtaining the combined aroma of several volatile substances by individually mixing the vapors of said substances with an odorless gas, blending the gas mixtures in a blending chamber and then determining the aroma of the blended mixtures.

14 Claims, 1 Drawing Figure

METHOD AND APPARATUS FOR OBTAINING THE COMBINED AROMA OF SEVERAL SUBSTANCES

This is a division of copending application Ser. No. 369,846 filed on Apr. 19, 1982, now U.S. Pat. No. 4,520,651.

This invention relates to the art of making flavors and perfumes, and more particularly, to a method and apparatus for blending different vapors to obtain a desired mixture.

BACKGROUND

In the arts of cooking and making of flavors it is well known that the human senses of smell and taste are very closely related. In cooking when a chef wants to check a certain dish he usually smells it before tasting it. Similarly a wine conoisseur smells the "bouquet" of a wine before sampling it.

In the art of making flavors, most staple ingredients are volatile. A flavorist who is trying to either create a new flavor or improve an existing one also used his sense of smell extensively. When his combination of ingredients has an acceptable aroma he knows that he is close to his target. However, in order to reach this point, the flavorist must actually mix the ingredients together before he can smell them. Some flavors require hundreds of ingredients. Furthermore, the amount of certain ingredients used in any given flavor is also critical for obvious reasons. Thus the process of flavor making is very long and painstaking.

One method that has been used to obviate the need for mixing the ingredients before smelling them is to dip a so-called smelling blotter in a bottle containing each ingredient and then placing them in close proximity to each other. The vapors from each ingredient mingle together. Obviously, this method may be used with only literally a handfull of ingredients. Furthermore, the method does not reveal any quantitative information.

The above considerations are vary applicable in the art of making frangrances.

SUMMARY OF THE INVENTION

A closed container which is only partially filled with a volatile liquid substance also contains the vapors of that substance disposed above the liquid. The invention presented herewith teaches a method and apparatus of obtaining the combined aroma of several liquid substances comprising the steps of mixing the vapors of each substance individually with an odorless gas; blending the gas mixtures so formed to obtain a composite gas and detecting the aroma of the composite gas.

The apparatus which is used to perform the above steps comprises a source of odorless gas, a plurality of closed containers which are partially filled with volatile substances, a first plurality of connecting means which supply odorless gas to the containers from the gas supply, a blending chamber and a second plurality of connecting means which allow the gas mixtures of odorless gas and vapors from each container into the blending chamber for blending.

DESCRIPTION OF THE PREFERRED EMBODIMENT

Figure 1:
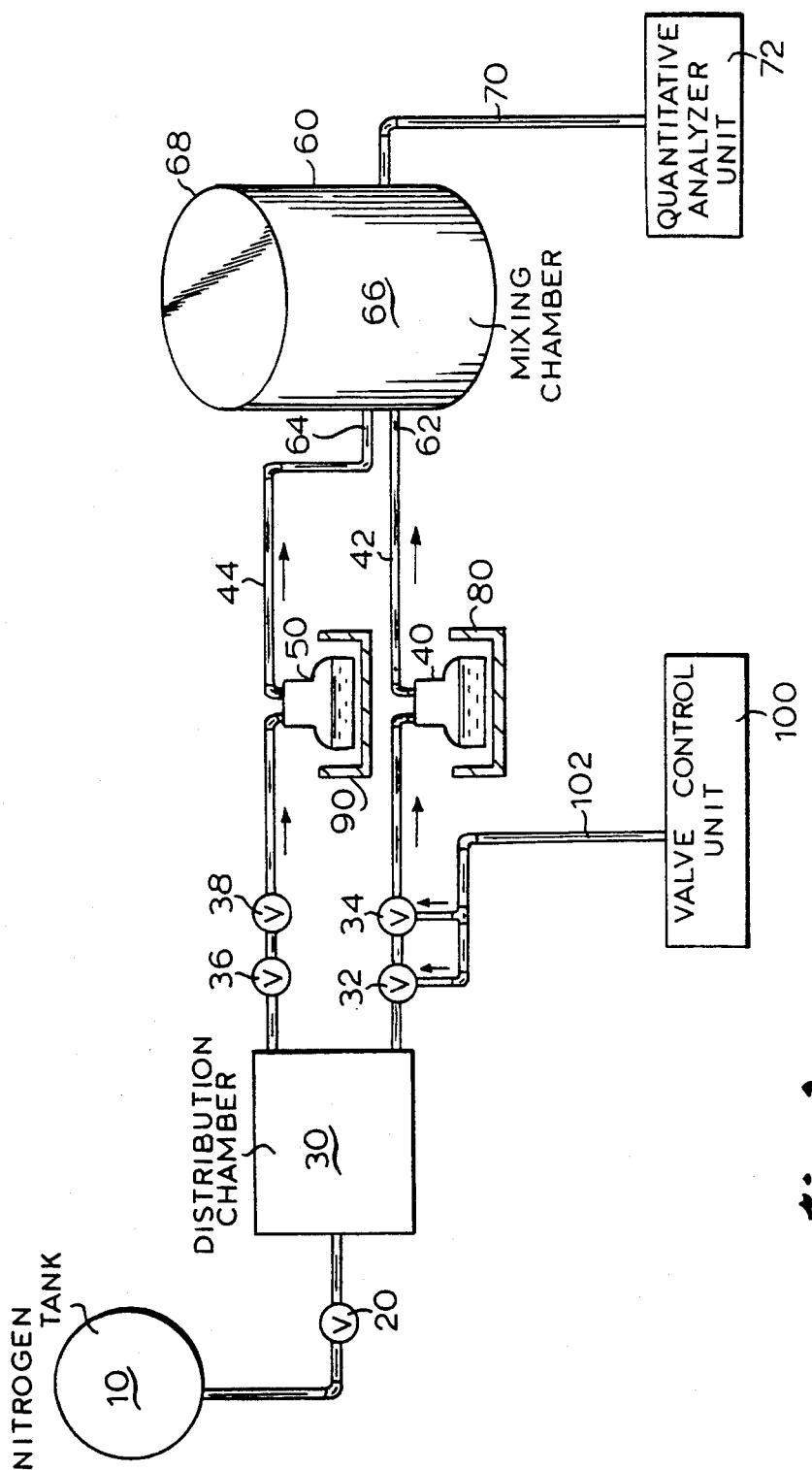
FIG. 1 shows the elements of the embodiments of the subject apparatus.

As shown in FIG. 1, a nitrogen tank 10 supplies nitrogen to a distrubution chamber 30 through a reducing valve 20, so that the pressure within the distribution chamber is about 5 lbs/sq. in. There are also a plurality of closed containers which hold the liquid ingredients that are used to make flavors or perfumes.

Each one of the containers is initially only partially filled with a given ingredient. Since each ingredient is volatile, a portion of the ingredient is always held by the container as a vapor. Although FIG. 1 shows only two such containers, 40 and 50 it is to be understood that a much larger number of containers is normally used as shown in the example given below.

Container 40 is supplied with nitrogen from the distribution chamber through a shut off valve 32 and an adjusting valve 34. The adjusting valve is provided to control the amount of nitrogen supplied to the container 40, and it has a vernier calibrated from 0.00 to 10.00, said vernier settings being proportional to the amount of gas flowing through the valve. The container 40 is also connected by pipe 42 to a mixing chamber 60. Preferrably pipe 42 is flexible.

Similarly container 50 is supplied with nitrogen through valves 36 and 38 and is connected to the blending chamber 60 by a pipe 44.

Blending chamber 60 has a tubular shape with a 2" in diameter and it is open at both ends. Pipes 42 and 44 are connected to the side wall of the blending chamber preferably near the lower end, as at 62 and 64.

In order to blend and smell the vapors of certain ingredients, the shutoff valves such as 32 and 34 are opened. Nitrogen flows into each of the selected containers and mixes with the vapors therein. The gas mixture then flows toward the blending chamber.

Normally the blending chamber rests on a flat surface which closes the bottom end 66. The gas mixtures from each pipe such as 42 and 44 blend in the blending chamber to form a composite gas whose aroma can be detected by smelling the top of the blending chamber. Since nitrogen is odorless only the effect of the selected ingredients is sensed.

Advantageously, the amount of any ingredient may be changed by changing the vernier setting of the respective adjusting valve. Before testing each new mixture, the blending chamber 60 is lifted and the old mixture is blown out through the bottom. Ingredients may be added or deleted by merely opening or closing the respective shutoff valves. Furthermore, the setting of each adjusting valve for a certain mixture can be recorded and thus, any mixture can easily be duplicated in the future.

In order to determine quantitavely the exact composition of a certain mixture of vapors, the mixture is fed via flexible pipe 70 to a quantitative analyzer unit 72. This unit may comprise a GLC, a mass-spectroscopy apparatus or other apparatus which can perform the desired quantitative analysis.

Using an apparatus built according to this invention, the following ingredients were combined to obtain a pineapple flavor:

| CONTAINER NUMBER | INGREDIENT | VERNIER SETTING |
|---|---|---|
| 1 | Allyl Caproate | 2.15 |

-continued

| CONTAINER NUMBER | INGREDIENT | VERNIER SETTING |
|---|---|---|
| 2 | Ethyl Heptanoate | 5.06 |
| 3 | Gamma Octalactone | 2.20 |
| 4 | Ethyl Acetate | 2.19 |
| 5 | Alpha Ionone | 1.05 |
| 8 | Ethyl Butyrate | 0.23 |
| 10 | Phenyl Ethyl Alcohol | 3.15 |
| 12 | Ethyl Maltol | 3.05 |
| 14 | Acetic Acid | 2.10 |
| 15 | Gamma Decalactone | 4.10 |
| 16 | Ethyl Hexanoate | 2.05 |
| 18 | Trans 2-Hexenyle Butyrate | 2.20 |
| 20 | Ethyl Benzoate | 2.22 |

If the apparatus is used for along time, the user's nose may dry out causing irritation. In order to prevent this, one of the closed containers can be used to hold water thus introducing water vapors into the blending chamber.

In addition to nitrogen other odorless gasses may be used as a mixing medium, such as air or an inert gas.

As previously stated, the ingredients held in the containers must be volatile. Since some liquids have a relatively low vapor pressure at room temperatures, these liquids may be placed in containers which have a heating jacket for heating the liquid thus increasing its vapor pressure. Other liquids have a relatively high vapor pressure, at standard room temperature and pressure, i.e. they may evaporate too fast. These liquids may be held in containers with cooling jackets such as the one shown for container 50. Such heating and cooling means are well-known in the chemical arts and need not be described here.

The shutoff and adjusting valves can be manual. Alternatively they may be of the type that can be controlled from a remote control unit such as 100 via control lines 102. The control unit can be of the mechanical, electrical or pneumatic types. Such control units are also well known in the chemical arts.

The shutoff and adjusting valve are shown in FIG. 1 as being disposed between the containers and the distribution chamber. However, they could also be disposed between the containers and the blending chamber.

The method and apparatus described herein can also be used to find a combination of ingredients which would mask partially or completely an undesirable odor. This could be accomplished by putting in one of the containers a substance or solution having the undesirable odor, and then mixing and blending the undesirable vapors with other vapors in accordance with the method outlined above, repetitively until the overall combination of gases has an inoffensive odor.

I claim:

1. An apparatus for obtaining the combined aroma of several volatile substances comprising:

a source of odorless gas;

a plurality of closed containers with the volatile substances disposed therein, said containers being only partially filled so that each container contain said volatile substance in liquid and vapor form;

a first plurality of connecting means for supplying odorless gas from the source to each of said containers;

a blending chamber; and a second plurality of connecting means connecting said containers to the blending chamber;

whereby the odorless gas supplied by the first connecting means mixes with the vapors contained in each container to form gas mixtures and whereby said gas mixtures flows via said second plurality of connecting means to the blending chamber where the mixtures form a gas composite with a determinable aroma.

2. The apparatus as claimed in 1 also comprising a shutoff valve in each of said first plurality of connecting means.

3. The apparatus as claimed in 2 also comprising an adjusting valve in each of said first plurality of connecting means.

4. The apparatus as claimed in 1 also comprising a shutoff valve in each of said second plurality of connecting means.

5. The apparatus as claimed in 4 also comprising an adjusting valve in each of said second plurality of connecting means.

6. The apparatus claimed in 5 wherein said shutoff and adjusting valves are controlled by a valve control unit.

7. The apparatus as claimed in 1 wherein the blending chamber has a tubular shape with two open ends.

8. The apparatus as claimed in 1 wherein the odorless gas is nitrogen.

9. The apparatus as claimed in 1 wherein the odorless gas is air.

10. The apparatus as claimed in 1 wherein the odorless gas is an inert gas.

11. The apparatus as claimed in 1 wherein at least one of the containers is provided with a heating means for increasing the volatility of the substance therein.

12. The apparatus as claimed in 1 wherein at least one of the containers is provided with cooling means for decreasing the volatility of the substance therein.

13. The apparatus as claimed in 1 wherein one of said containers contains water which provides water vapors to the blending chamber.

14. An apparatus for blending the vapors of a plurality of substances comprising:

a nitrogen tank a delivery chamber connected to said nitrogen tank through a pressure-regulating valve;

a plurality of a closed containers each one of said containers holding a volatile substance and a vapor of said liquid suspended thereabove;

a plurality of shutoff and adjusting valves which provide nitrogen from said delivery chamber to each of said containers;

a tubular blending chamber; and a plurality of flexible pipes connecting said containers to said blending chamber.

* * * * *